United States Patent
Collins

(10) Patent No.: US 9,655,644 B2
(45) Date of Patent: May 23, 2017

(54) MEDICAL DEVICE: LAPAROSCOPIC BAG

(75) Inventor: Justin Collins, Chertsey (GB)

(73) Assignee: ASHFORD & ST. PETER'S HOSPITALS, Chertsey, Surrey (GB)

(*) Notice: Subject to any disclaimer, the term of this patent is extended or adjusted under 35 U.S.C. 154(b) by 859 days.

(21) Appl. No.: 13/583,503

(22) PCT Filed: Mar. 7, 2011

(86) PCT No.: PCT/GB2011/050442
§ 371 (c)(1),
(2), (4) Date: Jan. 27, 2014

(87) PCT Pub. No.: WO2011/110836
PCT Pub. Date: Sep. 15, 2011

(65) Prior Publication Data
US 2014/0135788 A1    May 15, 2014

(30) Foreign Application Priority Data
Mar. 8, 2010 (GB) .................. 1003817.2

(51) Int. Cl.
*A61B 17/34* (2006.01)
*A61B 17/00* (2006.01)
*A61B 17/221* (2006.01)

(52) U.S. Cl.
CPC .... *A61B 17/3423* (2013.01); *A61B 17/00234* (2013.01); *A61B 17/221* (2013.01); *A61B 2017/00287* (2013.01); *A61B 2017/348* (2013.01); *A61B 2017/3486* (2013.01)

(58) Field of Classification Search
CPC .......... A61B 17/00234; A61B 17/3423; A61B 17/3431; A61B 17/3439; A61B 2017/00265; A61B 2017/00283; A61B 2017/3419; A61B 2017/3425; A61B 2017/3427; A61B 2017/3429; A61B 2017/3433; A61B 2017/3441; A61B 2017/3445; A61B 2017/3447; A61B 2017/345; A61B 2017/348; A61B 2017/3486; A61B 2017/3488; A61B 2017/3492
See application file for complete search history.

(56) References Cited

U.S. PATENT DOCUMENTS

| | | | | |
|---|---|---|---|---|
| 397,060 | A * | 1/1889 | Knapp | A61M 25/10 604/103.03 |
| 3,253,594 | A * | 5/1966 | Matthews | A61M 25/1009 604/103.03 |
| 3,459,175 | A * | 8/1969 | Miller | A61M 25/0108 600/431 |

(Continued)

FOREIGN PATENT DOCUMENTS

| | | |
|---|---|---|
| EP | 0 739 604 A1 | 10/1996 |
| GB | 2 371 991 A | 8/2002 |

(Continued)

*Primary Examiner* — David C Eastwood
(74) *Attorney, Agent, or Firm* — Venable LLP; Keith G. Haddaway; Kerri M. Patterson

(57) ABSTRACT

A laparoscopic bag, wherein the laparoscopic bag comprises one opening which is in a top portion, and a body portion, wherein the laparoscopic bag comprises an inner layer which is waterproof, a middle layer which is resistant to morcellation, and an outer layer which is waterproof.

8 Claims, 2 Drawing Sheets

(56) References Cited

U.S. PATENT DOCUMENTS

| | | | |
|---|---|---|---|
| 5,037,379 A | | 8/1991 | Clayman et al. |
| 5,368,545 A | * | 11/1994 | Schaller ................. A61B 46/23 128/846 |
| 5,611,803 A | | 3/1997 | Heaven et al. |
| 5,618,296 A | | 4/1997 | Sorensen et al. |
| 6,086,603 A | * | 7/2000 | Termin ............... A61B 17/3421 604/164.01 |
| 6,270,505 B1 | * | 8/2001 | Yoshida ........... A61B 17/00234 606/127 |
| 6,319,246 B1 | | 11/2001 | de la Torre et al. |
| 6,350,267 B1 | | 2/2002 | Stefanchik |
| 6,458,077 B1 | * | 10/2002 | Boebel ..................... A61B 1/12 600/114 |
| 7,691,089 B2 | * | 4/2010 | Gresham ............ A61B 17/3417 604/174 |
| 8,376,938 B2 | * | 2/2013 | Morgan ............. A61B 17/3423 600/204 |
| 8,419,635 B2 | * | 4/2013 | Shelton, IV ....... A61B 17/3423 600/208 |
| 8,821,377 B2 | * | 9/2014 | Collins ................ A61B 17/221 128/898 |
| 2004/0111061 A1 | * | 6/2004 | Curran ............... A61B 17/3421 604/174 |
| 2006/0211919 A1 | * | 9/2006 | Wilk .................. A61B 1/00082 600/207 |
| 2006/0241651 A1 | * | 10/2006 | Wilk .................. A61B 17/3423 606/108 |
| 2007/0135780 A1 | * | 6/2007 | Pagedas ........... A61B 17/00234 604/327 |
| 2007/0239108 A1 | * | 10/2007 | Albrecht ............ A61B 17/3415 604/96.01 |
| 2008/0103508 A1 | | 5/2008 | Karakurum |
| 2009/0036745 A1 | * | 2/2009 | Bonadio ............ A61B 17/3423 600/208 |
| 2009/0221960 A1 | * | 9/2009 | Albrecht ............ A61B 17/3421 604/103.03 |
| 2009/0299137 A1 | * | 12/2009 | Gal ...................... A61B 1/0607 600/109 |
| 2010/0312066 A1 | * | 12/2010 | Cropper ............ A61B 17/3423 600/207 |
| 2011/0011410 A1 | * | 1/2011 | Desai ................ A61B 17/0293 128/898 |
| 2012/0253134 A1 | * | 10/2012 | Smith ................ A61B 17/3423 600/203 |

FOREIGN PATENT DOCUMENTS

| | | |
|---|---|---|
| WO | WO-2009/117435 A2 | 9/2009 |
| WO | PCT/GB2011/050442 | 11/2011 |

* cited by examiner

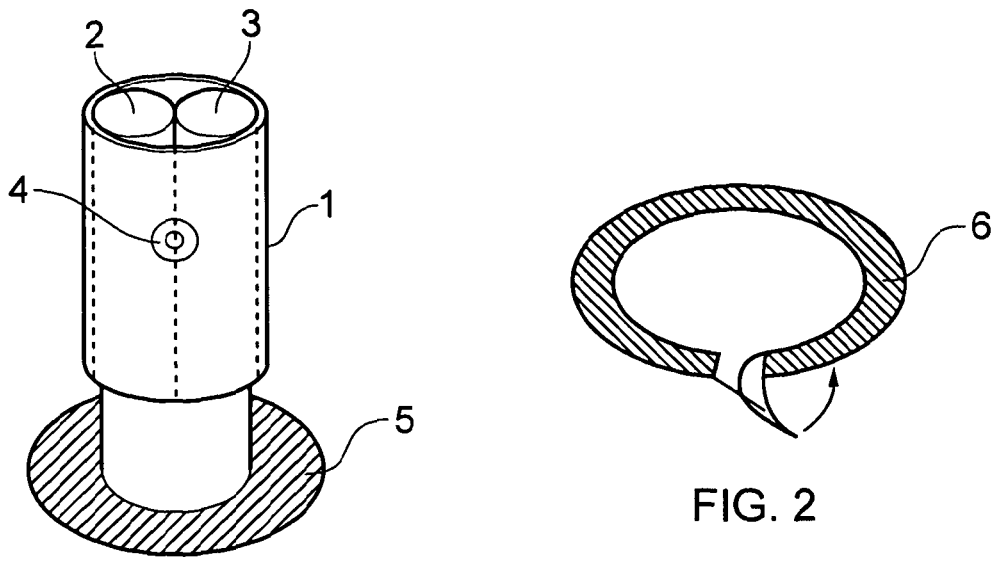
FIG. 1
FIG. 2
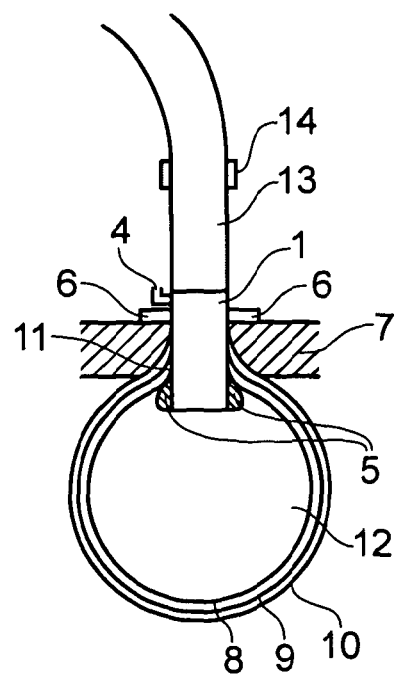
FIG. 3

MEDICAL DEVICE: LAPAROSCOPIC BAG

CROSS REFERENCE TO RELATED APPLICATIONS

This application is the U.S. National Stage under 35 U.S.C. §371 of International Application No. PCT/GB2011/050442 filed on Mar. 7, 2011, which claims the benefit of Great Britain Patent Application No. 1003817.2 filed on Mar. 8, 2010, the disclosures of which are hereby incorporated by reference.

FIELD OF THE INVENTION

The present invention relates to a laparoscopic bag, a laparoscopic port and a sheath and in particular to their use in laparoscopic surgery. The invention also relates to a method of laparoscopic surgery that involves the medical device, and to a method of using the medical device.

BACKGROUND OF THE INVENTION

Laparoscopic surgery, also known as minimal access, minimally invasive or keyhole surgery, is a modern surgical technique. During laparoscopic surgery operations are performed through small incisions, usually 0.5 to 1.5 cm in length. This is in contrast to traditional open surgery where a much longer incision would be made to perform the same operation.

Laparoscopic surgery is becoming increasingly popular, with more and more routine operations such as nephrectomy and cystectomy being carried out with this type of surgery.

Laparoscopic surgery has many advantageous over traditional surgery, which are mainly due to its minimally invasive nature and small incision length. These advantages include reduced pain, reduced blood loss, reduced scarring, fewer post-operative infections and shorter recovery times.

However, one of the limitations of laparoscopic surgery concerns the removal of a relatively large specimen. This is particularly common in oncological procedures such as laparoscopic radical nephrectomy, colectomy, cystectomy and hysterectomy. In most oncological and many other laparoscopic procedures, the specimen to be removed from the patient's body is too large to be able to remove it easily through the normal incision made for a laparoscopic port (called a port incision). In this situation the surgeon currently has two options.

The first option is to make a further, larger, incision or to enlarge the port incision so that the specimen can be removed as a whole. Usually this requires an incision of 10 cm long or longer, and sometimes the incision can be as long as 20 cm. Hence, this reduces the advantages of using laparoscopic surgery, which are listed above, and in some cases means that there is actually minimal benefit in performing laparoscopic surgery, over traditional open surgery.

The second option is to morcellate the specimen inside the body cavity into pieces that are small enough to be removed through the port incision. A major concern with this approach is that it is not always possible to ensure that every trace of the morcellated specimen is removed. Where the specimen is benign, leaving a part of the specimen in the body cavity may lead to infection as the tissue breaks down and acts as a source for infection. There is even more risk involved in this method when the specimen is malignant, since any escape of malignant cells can lead to tumour seeding. Tumour seeding can occur at the site from which the specimen is removed. In addition, since the surgical plume travels throughout the surgical site, metastasis can occur at any point where 'raw' areas are, such as any of the port sites.

There have been some attempts to reduce the risks associated with morcellating the specimen inside the body cavity, by placing a bag around the specimen before it is morcellated. Such a device is generally known as an Endo-Bag. Endo-Bags normally comprise a plastic bag, with an opening at one end. They are inserted through the port incision, the specimen, is then passed into the bag and can be pulled through the incision in the bag, optionally after being cut up. Some Endo-Bags, such as that shown in U.S. Pat. No. 6,270,505 comprise a plastic tube with an opening at both ends. A drawstring is provided at one end, which is closed once the specimen is inside the tube. Most large specimens are still extracted in one piece through a separate incision. The most common type of morcellation is via a blunt instrument which crushes the tissue and it is then pulled out in pieces through the smaller incision the bag sits in. Morcellation using devices with rotating blades and suction is becoming increasingly common.

While the use of Endo-Bags can reduce the risks, Endo-Bags do not enclose the whole surgical plume, particularly when they are closed only by means of a drawstring at one end. Therefore, the risk of tumour seeding and port site metastasis remains. In addition, Endo-Bags are normally made from one or two layers of a thin flexible film of a polymer such as polyethylene or polyurethane. These can be ruptured by a sharp instrument, including those needed to morcellate the specimen. This possibility also presents the danger of tumour seeding.

The present invention is concerned with addressing these problems and with providing an improved solution for the removal of large specimens during laparoscopic surgery. In particular, the present invention aims to provide a device for use in minimal access surgery, and a method of laparoscopic surgery which allows for morcellation of a specimen inside the body cavity, without the risk of tumour seeding.

SUMMARY OF THE INVENTION

A first aspect of the invention provides a laparoscopic bag, wherein the laparoscopic bag comprises one opening which is in a top portion, and a body portion, wherein the laparoscopic bag comprises an inner layer which is waterproof, a middle layer which is resistant to morcellation, and an outer layer which is waterproof.

A second aspect of the invention provides a laparoscopic port that comprises tubular housing, an inflatable cuff around the distal end of the housing, an insufflation nozzle which is in fluid communication with the inflatable cuff and a locking ring, which can be passed over the proximal end of the housing, and secured relative to the housing at different points along the length of the housing.

A third aspect of the invention provides a sheath comprising a tube of medical-grade waterproof material that has at one end attaching means for attaching it to a laparoscopic bag for use during laparoscopic surgery.

A fourth aspect of the invention provides a kit comprising a laparoscopic bag according to the first aspect of the invention, and a sheath according to the third aspect of the invention.

A fifth aspect of the invention provides a method of carrying out laparoscopic surgery to remove a specimen from the body of a patient, the method comprising the steps of:

(i) providing a laparoscopic port and positioning the laparoscopic port through the skin of the patient so that the distal end of the laparoscopic port is in a body cavity and the proximal end of the laparoscopic port is outside the patient;

(ii) providing a laparoscopic bag according to any of claims 1 to 6, and passing the laparoscopic bag through the laparoscopic port into the body cavity;

(iii) placing the specimen into the body portion of the laparoscopic bag;

(iv) passing the top portion of the laparoscopic bag through the laparoscopic port;

(v) passing a morcellator through the top portion of the laparoscopic bag, morcellating the specimen in the body portion of the laparoscopic bag; and (vi) removing the morcellated specimen from the body of the patient through the top portion of the laparoscopic bag.

A sixth aspect of the invention provides the use of a laparoscopic bag according to the first aspect of the present invention, a laparoscopic port according to the second aspect of the invention, a sheath according to the third aspect of the invention, and/or a kit according to the fourth aspect of the invention, in laparoscopic surgery to remove a specimen from the body of a patient.

The laparoscopic bag of the present invention addresses the problems associated with the removal of large specimens from the body during laparoscopic surgery by comprising three layers and by comprising one opening only, and thereby allows for morcellation of the large specimen within the body cavity, without risk of tumour seeding.

The use of a three-layered bag with an inner layer that is waterproof, a middle layer which is resistant to morcellation, and an outer layer which is waterproof, is highly advantageous since it provides an enclosed environment for safe morcellation of large specimens from which traces of specimen cannot escape. In previous Endo-Bags with two waterproof layers there is a risk that the layers will be ruptured by a sharp instrument, such as that needed to morcellate the specimen. However, with the laparoscopic bag of the present invention, the middle layer is resistant to morcellation, so will not be ruptured during normal use. Therefore, even if the inner layer is ruptured, the outer layer will be protected from rupture by the middle layer and will still provide an enclosed environment from which traces of the specimen cannot escape.

In addition, having only one opening, which is in the top portion, means that when the top portion is passed out of the body cavity through a port, the body portion of the laparoscopic bag that remains in the body will be entirely enclosed. The laparoscopic bag is not vulnerable to rupture due to the three layers so provides an environment that is safe for morcellation. This represents a significant advantage over previous Endo-Bags that comprise a tube with a drawstring closure at one end.

The fact that the laparoscopic bag of the present invention allows for the safe morcellation of a large specimen in the body cavity means that laparoscopic surgery can be carried out using this bag without either having to make a large incision to remove a specimen, or risking tumour seeding. This represents a significant advance in medical technology and will bring widespread patient benefits, meaning that patients can benefit fully from the advantages of minimally invasive laparoscopic surgery, without risking tumour seeding or port-site metastasis.

In more detail, the laparoscopic bag comprises a top portion and a body portion, which are defined in that there is an opening in the top portion, but not in the bottom portion. It is preferred that the bag comprises a rectangular shape when flat, and a tubular shape when open, with one end sealed. The body portion is the section of the bag adjacent the sealed end, with the top portion being the section of the bag at the end which comprises the opening. Having a rectangular shaped bag is advantageous since, during use, the bag can be rolled up and passed through a laparoscopic port. A rectangular shaped bag is able to be rolled up neatly and efficiently in terms of space, compared to a bag of another shape.

The top portion will, during use, become neck-shaped as a result of the top of the bag being pulled back through the port after the bag is opened. Where the cross-sectional area of the body portion and top portion is the same, which is preferred, the bag can be a tubular shape. When in use, the top portion is approximately tubular, and the body portion shape is caused by the specimen and the pressure differences caused by the morcellation process.

As noted above, the top portion of the laparoscopic bag comprises an opening. This is the only opening in the bag, there are no other openings.

The laparoscopic bag of the present invention comprises three layers. The inner and outer layers are waterproof, and can be made of any suitable material. The inner and outer layers are usually made from a thin flexible film of a polymer such as polyethylene or polyurethane. The inner and outer layers can be made of the same or different material from one another. Such films are well known to the person skilled in the art. The inner layer may be white in colour to reflect light and aid visibility when the bag is in use in the body cavity.

The middle layer may be brightly coloured, for example an unnatural luminous colour which could be orange or green, so that if the white inner layer is breached the colour of the middle layer shows through and it is evident that the inner layer has been breached. The middle layer is resistant to morcellation. By this we mean that the middle layer is made of a material that can not be penetrated by the morcellation process carried out by a morcellator of the type used in laparoscopic surgery which can mean an electric motorised morcellator or a hand held device that is used to break down the specimen.

Any material that is resistant to morcellation can be used as the middle layer. Suitable materials for use as the middle layer that are resistant to morcellation include a woven mesh of synthetic material such as polyurethane, a film or mesh of heavy-duty plastic, a mesh of metallic wires or a mesh of carbon fibres. In a preferred embodiment, the middle layer comprises a mesh.

With the laparoscopic bag of the invention, if the inner layer is ruptured, the middle layer will protect the outer layer from also being ruptured, so the specimen will still be enclosed as noted above. It would, however, be advantageous for the surgeon to know that the inner layer has been ruptured, so that they can document the incident, check the outer layer, and ensure that there has been no escape of the specimen. Accordingly, in a preferred embodiment of the invention the inner layer is white and the middle layer is coloured, textured, or patterned or the middle layer is transparent and the outer layer is coloured, textured, or patterned. This means that if in inner layer is ruptured, the middle layer or the outer layer will be visible to a camera which is usually used during laparoscopic surgery, to enable the surgeon to take appropriate action. Preferably the middle layer is brightly coloured, most preferably luminous green or the middle layer is transparent and the outer layer is brightly coloured, preferably luminous green.

The present invention also relates to a sheath, in particular a sheath that has at one end attaching means for attaching it to a laparoscopic bag for use during laparoscopic surgery. This is advantageous, since the sheath can be attached to the neck of a laparoscopic bag so that a morcellated specimen can be removed through the neck of the bag, and through the sheath that will enable safe transportation of the specimen and the whole surgical plume away from the patient.

The sheath of the present invention comprises a tube of medical-grade waterproof material. By medical grade, we mean suitable for use in medical applications, such as laparoscopic surgery. The waterproof material can be the same as the waterproof material used for the inner and outer layers of the laparoscopic bag or can be different.

The sheath material should be such that it acts as an effective barrier keeping the surgical plume within the bag and sheath. The surgical plume consists of small particles, tumour cells, liquids, aerosols and any other materials including biological materials that may move out of the bag during the laparoscopic procedure and specimen removal.

The sheath has at one end attaching means for attaching it to a laparoscopic bag for use during laparoscopic surgery. Any suitable attaching means can be used that maintain a waterproof connection between the sheath and the laparoscopic bag. In one preferred embodiment, the attaching means is either a ridge that is capable forming a zip-lock fit with housing on a laparoscopic bag, or housing that is capable of forming a zip-lock fit with a ridge on a laparoscopic bag i.e. a freezer-bag style attachment. In another preferred embodiment, the attaching means could be adhesive such that the sheath opening and the bag opening both have an adhesive strip which is made accessible after pulling off protective tape. The sheath and the bag are sealed by pressing the adhesive strips together. In another preferred embodiment, the attaching means could be through locking rings such as in an embroidery hoop where both the sheath and the bag are secured between two rings of only slightly different circumference which are then tightened and locked in place by a screw or other locking mechanism.

When a sheath is used, the laparoscopic bag also has attaching means on the top portion which cooperate with the attaching means on the sheath. As above, in a preferred embodiment the laparoscopic bag has attaching means that comprises either a ridge that is capable of forming a zip-lock fit with housing on a sheath, or housing that is capable of forming a zip-lock fit with a ridge on a sheath.

According to the third aspect the present invention relates to a laparoscopic port. This can advantageously be used with the laparoscopic bag of the present invention to secure the bag in place in the body during a laparoscopic procedure.

The laparoscopic port comprises tubular housing often with two ports with an oval cross section. One port is used for the morcellator and the other is used for irrigation. Laparoscopic ports are known in the art, as they are used in all laparoscopic operations. Accordingly, the basic housing of a port is well known to a person skilled in the art.

The tubular housing of the port of the present invention is preferably oval, and can be anything from 5 mm to 4 cm along the longest diameter, but is preferably around 2 cm along the longest diameter.

The tubular housing has an inflatable cuff around the distal end of the housing and an insufflation nozzle which is in fluid communication with the inflatable cuff. By distal end of the housing we mean the end portion, usually the end third, that would be furthest into the patient during an operation. By the proximal end we mean the end portion, usually the end third, that would be furthest away from the patient during an operation.

When inflated, the inflatable cuff resembles a ring around the outside of the distal end of the housing, that can abut the tissue between the abdominal cavity and the skin through which the housing is inserted.

The laparoscopic port of the present invention may also comprise a locking ring, which can be passed over the proximal end of the housing, and secured relative to the housing at different points along the length of the housing with a ring which overlaps and then locks in place with a clasp similar to a watch bracelet clasp.

The locking ring is positioned relative to the inflatable cuff so that they grip the skin, thereby securing the housing in place. The advantage of having an adjustable locking ring is to secure it to provide a tight seal in patients with varying depths of subcutaneous fat or abdominal muscle so that the bag is secured and the irrigation part of the morcellation process can be enclosed within the bag.

The laparoscopic port preferably comprises two channels running through the length of the housing. Instrumentation such as a morcellator, irrigator and camera can be passed through the channels. It is preferred that the channels are removable from the housing, so that they can be removed leaving the oval shaped frame of the housing, to allow bigger objects, such as a rolled-up laparoscopic bag, to pass through the port.

The present invention also relates to a kit comprising the laparoscopic bag according to the first aspect of the invention and the sheath according to the third aspect of the invention, as well as optionally a laparoscopic port according to the second aspect of the invention. The kit is preferably provided as a single use disposable kit. The laparoscopic bag is preferably in a collapsed state in the kit ready for use and is most preferably rolled up.

The present invention also relates to a method of carrying out laparoscopic surgery to remove a specimen from the body of a patient, as set out above. The method comprises the following steps.

(i) Providing a laparoscopic port and positioning the laparoscopic port through the skin of the patient so that the distal end of the laparoscopic port is in a body cavity and the proximal end of the laparoscopic port is outside the patient. Any laparoscopic port can be used, but it is preferred that a port according to the second aspect of the invention is used.

(ii) Providing a laparoscopic bag according to the first aspect of the invention, and passing the laparoscopic bag through the laparoscopic port into the body cavity. When a laparoscopic port according to the present invention with removable channels is used, the channels can be removed before the bag is passed through.

(iii) Placing the specimen into the body portion of the laparoscopic bag. This is done using conventional manipulation devices. A camera is provided on the laparoscopic equipment, so that the surgeon can see the specimen and guide it into the bag.

(iv) Passing the top portion of the laparoscopic bag through the laparoscopic port.

(v) Passing a morcellator through the top portion of the laparoscopic bag, and morcellating the specimen in the body portion of the laparoscopic bag. A conventional morcellator is used for this step. In a preferred embodiment the specimen is irrigated under low pressure during morcellation, by circulating a fluid around the bag. This causes the bag to gently inflate and the specimen to float and rotate in the irrigation fluid and keeps it away from the sides of the bag.

This is an important safety feature, as it makes it less likely for the inner layer of the bag to be ruptured by the morcellator. When the laparoscopic port comprises two channels, the morcellator with the camera is passed through one channel, and an irrigator is passed through the other channel. The specimen is morcellated until it is small enough to be removed via the port site.

(vi) Removing the morcellated specimen from the body of the patient through the top portion of the laparoscopic bag.

In a preferred embodiment, the method additionally comprises the step of attaching the top portion of the laparoscopic bag to one end of a sheath according to the third aspect of the invention, so that the morcellated specimen is removed from the body of the patient through the top portion of the laparoscopic bag and the sheath.

In a preferred embodiment, where a laparoscopic port according to the second aspect of the invention is used, the method preferably additionally comprises the steps of; removing the laparoscopic port from the patient's body once the top portion of the laparoscopic bag has passed through it in step (iv); inserting the laparoscopic port back inside the top portion of the laparoscopic bag so that the distal end of the housing is in the body cavity; inflating the inflatable cuff using the insufflation nozzle; passing the locking ring over the proximal end of the housing; and locking the locking ring against the housing so that the tissue between the abdominal cavity and the skin of the patient is gripped between the inflatable cuff and the locking ring.

The present invention also relates to the use of a laparoscopic bag according to the first aspect of the invention, a laparoscopic port according to the second aspect of the invention, a sheath according to the third aspect of the invention and/or a kit a according to the fourth aspect of the invention, in laparoscopic surgery to remove a specimen from the body of a patient.

BRIEF DESCRIPTION OF THE DRAWINGS

Embodiments of the invention will now be described with reference to the accompanying drawings, in which:

FIG. 1 shows a perspective view of a laparoscopic port according to a preferred embodiment of the present invention;

FIG. 2 shows a perspective view of a locking ring according to a preferred embodiment of the present invention;

FIG. 3 shows a cross sectional view of a laparoscopic bag and a laparoscopic port according to a preferred embodiment of the present invention;

DETAILED DESCRIPTION OF EMBODIMENT(S)

FIG. 1 shows the tubular housing 1 of a laparoscopic port, through which there are two channels, 2 and 3. The housing 1 is oval in cross section, with a largest diameter of around 20 cm. The housing has an insufflation nozzle, 4, at its proximal end which is in fluid communication with the inflatable cuff, 5. The locking ring 6, shown in FIG. 2, can be passed over the proximal end of the housing 1 and secured next to the skin 7, as shown in FIG. 3. The function of the port is to make a watertight seal around the incision and to hold the bag in place and allow access for the morcellator, tools for morcellation and irrigation.

Figure 4:
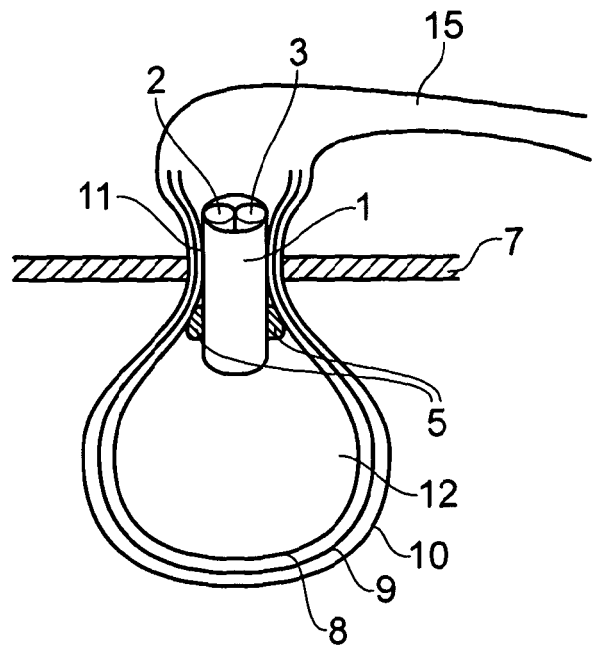
FIG. 4 shows a schematic view of a laparoscopic bag, a sheath and a laparoscopic port according to a preferred embodiment of the present invention.
Figure 5:
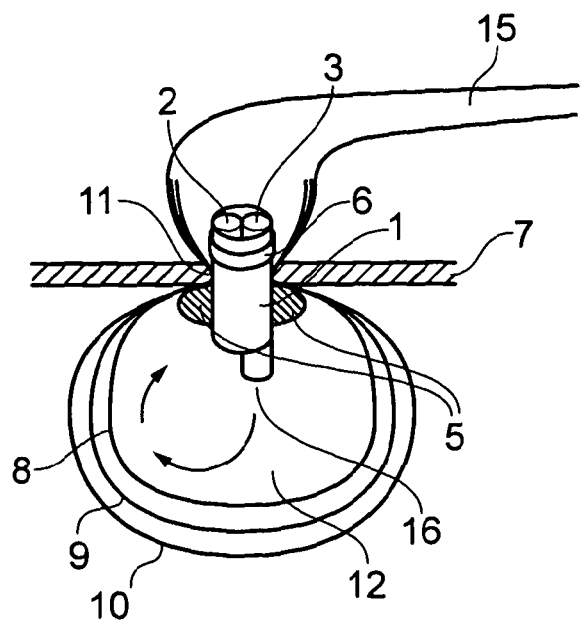
FIG. 5 view of a laparoscopic bag, a sheath and a laparoscopic port according to a preferred embodiment of the present invention.

FIGS. 3, 4 and 5, show the laparoscopic bag of a preferred embodiment of the present invention with inner layer 8, middle layer 9, and outer layer 10.

In FIGS. 3, 4 and 5, the laparoscopic port housing 1 is through the skin 7 of a patient and inside the top portion 11 of the laparoscopic bag. The laparoscopic bag body portion 12 is substantially spherical. The inflatable cuff 5 is inflated. In FIGS. 3 and 5, the locking ring 6 is in place against the skin, so that the inflatable cuff 5 and the locking ring 6 grip the skin 7 and hold the port housing 1 in place.

In FIG. 3 the port housing 1 is attached to a retrieval tube 13 which allows for endoscope and morcellator access to the specimen (not shown). This is in addition to the sheath. The retrieval tube has a waterproof quick attach/release joint 14 which is used after the edges of the bag are out of the incision site and the port is put in place.

In FIGS. 4 and 5 the outer layer 10 of the laparoscopic bag is attached to the sheath 15. During use, the laparoscopic bag 11 12 would be passed through the port housing 1 in collapsed form, usually rolled up, and opened inside the body cavity. The specimen, not shown, would be inserted through the top portion 11 and into the body portion 12. The port would then be removed, and reinserted inside the top portion 11 of the laparoscopic bag. The inflatable cuff 5 would be inflated, and the locking ring 6 secured over the housing, so as to grip the skin 7. A morcellator not shown would be passed through one of the channels 2 3 of the housing 1 and an irrigator 16 would be passed down the other channel. Irrigation would ensure that the specimen floats and is rotated and kept away from the inner wall 8 of the laparoscopic bag, as shown by the arrows in FIG. 5, while the specimen is morcellated.

Although the invention has been described above with reference to one or more preferred embodiments, it will be appreciated that various changes or modifications may be made without departing from the scope of the invention as defined in the appended claims.

The invention claimed is:

1. A laparoscopic port that comprises a tubular housing, an inflatable cuff around the distal end of the housing, an insufflation nozzle which is in fluid communication with the inflatable cuff, and an adjustable locking ring, which can be passed over the proximal end of the housing and positioned at different points along the length of the housing to overlap and lock in place at a point on the length of the housing in which the adjustable locking ring and inflatable cuff grip skin of a patient, wherein the laparoscopic port functions to make a watertight seal around an incision in a patient, wherein the laparoscopic port additionally comprises two channels running through the length of the housing and wherein the channels are removable from the housing.

2. The laparoscopic port of claim 1, wherein the port is for use with a laparoscopic bag.

3. A kit comprising a laparoscopic bag comprising one opening which is in a top portion, and a body portion, wherein the laparoscopic bag comprises an inner layer which is waterproof, a middle layer which is resistant to morcellation, and an outer layer which is waterproof, a sheath comprising a tube of medical-grade waterproof material that has at one end attaching means for attaching it to a laparoscopic bag and additionally comprising the laparoscopic port of claim 1.

4. The kit according to claim 3, which is provided as a single use disposable kit.

5. A method of carrying out laparoscopic surgery to remove a specimen from the body of a patient, the method comprising the steps of:
   (i) providing a kit according to claim 3;
   (ii) positioning the laparoscopic port through the skin of the patient so that the distal end of the laparoscopic port is in a body cavity and the proximal end of the laparoscopic port is outside the patient;
   (iii) passing the laparoscopic bag through the laparoscopic port into the body cavity;
   (iv) placing the specimen into the body portion of the laparoscopic bag;
   (v) passing the top portion of the laparoscopic bag through the laparoscopic port;
   (vi) passing a morcellator through the top portion of the laparoscopic bag, morcellating the specimen in the body portion of the laparoscopic bag; and
   (vii) removing the morcellated specimen from the body of the patient through the top portion of the laparoscopic bag.

6. The method of claim 5, additionally comprising the step of attaching the top portion of the laparoscopic bag to one end of the sheath so that the morcellated specimen is removed from the body of the patient through the top portion of the laparoscopic bag and the sheath.

7. The method of claim 5, wherein the method additionally comprises the steps of:
   removing the laparoscopic port from the patient's body once the top portion of the laparoscopic bag has passed through it in step (v);
   inserting the laparoscopic port inside the top portion of the laparoscopic bag so that the distal end of the housing is in the body cavity;
   inflating the inflatable cuff using the insufflation nozzle;
   passing the locking ring over the proximal end of the housing; and
   locking the locking ring against the housing so that the skin of the patient is gripped between the inflatable cuff and the locking ring.

8. the method of claim 5, wherein in step (vi) the specimen is irrigated during morcellation, and in step (vi) the morcellator is passed through one channel of the laparoscopic port and an irrigator is passed through the other channel of the laparoscopic port.

* * * * *